(12) United States Patent
Freeman et al.

(10) Patent No.: US 6,277,588 B1
(45) Date of Patent: Aug. 21, 2001

(54) SCREENING OF CELL POPULATIONS

(75) Inventors: Amihay Freeman, Ben-Shemen (IL); George Georgiou, Austin, TX (US)

(73) Assignee: Tel Aviv University (IL)

( * ) Notice: Subject to any disclaimer, the term of this patent is extended or adjusted under 35 U.S.C. 154(b) by 0 days.

(21) Appl. No.: 09/090,531

(22) Filed: Jun. 4, 1998

Related U.S. Application Data

(60) Provisional application No. 60/083,790, filed on May 1, 1998.

(51) Int. Cl.[7] .................................................. C12Q 1/24
(52) U.S. Cl. ................................ 435/30; 435/29; 435/34
(58) Field of Search .............................. 435/29, 30, 34, 435/182, 252.3, 320.1

(56) References Cited

U.S. PATENT DOCUMENTS

| | | | |
|---|---|---|---|
| 4,649,109 | * | 3/1987 | Perlman .................................. 435/30 |
| 4,801,529 | * | 1/1989 | Perlman .................................. 435/5 |
| 5,326,691 | * | 7/1994 | Hozier ..................................... 435/6 |
| 5,707,798 | * | 1/1998 | Brann ...................................... 435/6 |
| 5,792,617 | * | 8/1998 | Rotman ................................. 435/7.23 |

FOREIGN PATENT DOCUMENTS

WO 95/24648 * 9/1995 (WO) .

OTHER PUBLICATIONS

Schneider S. Magnetic Selection of Transiently Transfected Cells. biotechniques 21(5)876–880, May 1996.*

Winson M. If You've Got It, Flaunt It—Rapid Screening for Microbial Biocatalysts. Trends in Biotechnology 15:120–122, 1997.*

Sahar E. Flow Cytometric Analysis of Entire Microbial Colonies. Cytometry 15:213–221, 1994.*

Felix H. Enhanced Stability of Enzymes in Permeabilized and Immobilized Cells. Biotechnology Letters 4(3)181–186, 1982.*

Hopcroft D W Adult Rat Pancreatic Islet Cells Adherent to Microcarrier Beads. In Vitro Cellular & Developmental Biology 21(9)485–487, Sep. 1985.*

Till G A Two Strategies to Prepare Neural Cortical Cytoskeleton Components for the Generation of Monoclonal Antibodies. European J of Cell Biology 67:218–226, Jul. 1995.*

Maroudas N G Anchorage Dependence. Experimental Cell Research 74:337–342, 1972.*

Nir R. Flow Cytometric Isolation of Growth Rate Mutants: A Yeast Model. J of Microbiological Methods 14:247–256, 1992.*

\* cited by examiner

*Primary Examiner*—Ralph Gitomer
(74) *Attorney, Agent, or Firm*—Schnader Harrison Segal & Lewis LLP

(57) ABSTRACT

A method for screening large cell populations for isolation of mutants that express a target activity. The products of the screening method are disclosed. Various activities, including enzymatic activities can be selected.

17 Claims, 4 Drawing Sheets

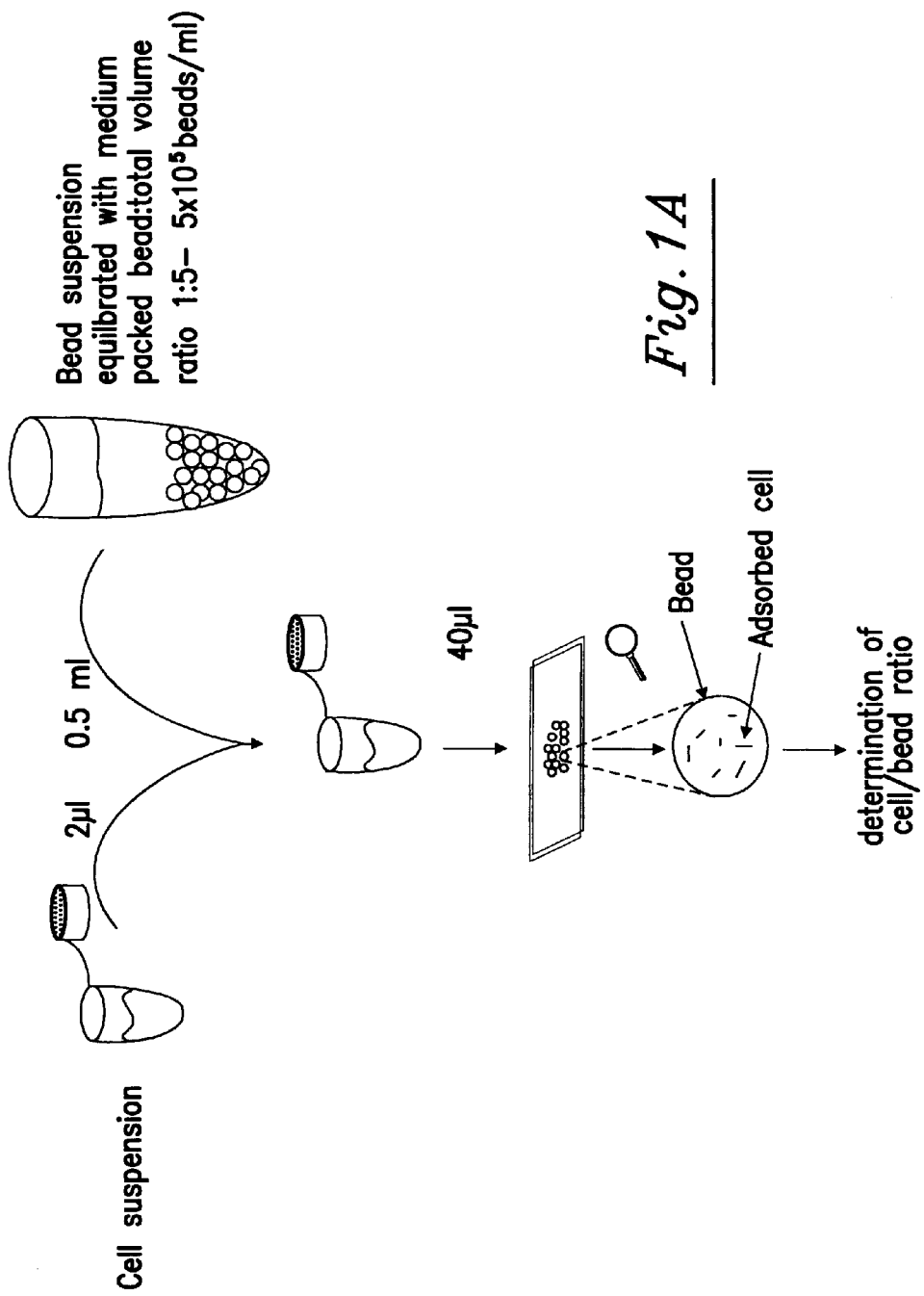

SCREENING OF CELL POPULATIONS

RELATED PATENT APPLICATIONS

This patent application is related to provisional patent application filed under 37 C.F.R. § 1.53(b)(2) on May 1, 1998, Ser. No. 60/083,790.

BACKGROUND OF THE INVENTION

1. Field of the Invention

The invention generally relates to screening of large cell populations e.g. bacteria, yeast, fungi or mammalian cells, for the isolation of mutants expressing envisaged or a target activity like an enzymatic activity. More particularly, the invention relates to screening of expression libraries for the isolation of rare mutants expressing enzymatic activity catalysing non-biological chemical reactions or enzymes with altered specificity.

2. Description of Related Art

The isolation of novel biocatalysts has been based for many years on screening of cell cultures derived from natural and artificial environments affecting selective pressure, resulting in the generation of enzymes exhibiting envisaged special activity and stability (P. S. J. Cheetham, 1987. Screening for new biocatalysts. Enzyme and Microbial Technology, 9, 194–213). The isolation of useful enzymes, such as proteases, lipases and esterases, was carried out by a multi-step screening including enrichment for target microorganisms, screening for desired activity and secondary screening for the isolation of enzyme overproducers. These screenings were traditionally based on spreading a diluted sample of the cell population to be screened on solid agar, including appropriate growth medium, in petri dishes. Colonies expressing the envisaged activity were isolated on the basis of selection pressure affected by the medium composition employed or by adding substrate and following observable changes e.g. colour development or clear zones on turbid background. Some of these methods were automated into robotic screening (D. B. Steele and M. D. Stowers, 1991. Techniques for selection of industrially important microorganisms. Annual Reviews in Microbiology, 45, 89–106). More recently, the application of flow cytometry to mutant selection and industrial strain improvement was successfully employed in a number of cases. Single cells were encapsulated within small e.g. 30 $\mu$ agar microbeads, allowed to proliferate into micro-colonies and the microbead population screened for enzymatic activities resulting in the production of fluorescence by flow cytometer (E. Sahar, R. Nirand R. Lamed, 1994. Flow cytometric analysis of entire microbial colonies. Cytometry, 15, 213–221.

However, the entrapment of cells and the subsequent propagation of these cells to form colonies within microbeads composed of polysaccharides is a complicated process. In addition, the screening and detection of desired mutants requires that a fluorescent or colored product accumulates within the microbead. Thus, special measures must be taken to retain the fluorescent/colored product. For example, the product must either be insoluble in the medium in which the reaction is carried out, or alternatively must be immobilized within the microbead to prevent its diffusion into the surrounding medium. Finally, the method of Sahar et al. requires very expensive instrumentation, e.g., a flow cytometer, and specially trained personnel to operate the instrument, both of which decrease the general applicability of the overall approach. The method of the invention overcomes these prior art disadvantages by immobilizing cells directly onto the surface of derivitized microbeads, which are subsequently immobilized as a monolayer on a solid surface which in a method that requires no special processing steps. The substrate used for the screening and detection of desired target cells or colonies is not subject to the solubility constraints of the method of Sahar et al., since the detection can be performed visually after the solvent is removed from the solid surface containing the immobilized microbeads. In addition, the detection method only requires simple and relatively inexpensive instrumentation that is present in, or readily available to any laboratory, e.g., a microscope, to identify the target cells/colonies.

A major objective in the field of applied biocatalysis is the identification or creation of enzymes capable of catalysing chemical, non-biological reactions. Although in some cases enzymes exhibiting activity on a broad spectrum of substrates were found capable of catalysing chemical reactions of similarly structured unnatural substrates (C. H. Who and G. M. Whitesides, 1994. Enzymes in organic synthesis. Pergamon Press), the systematic generation of new enzymes for this purpose remained a major challenge.

Recent developments in the field of genetic engineering and, in particular, options of introducing either predetermined or random changes into isolated genes by PCR created new tools for the generation of improved enzymes. A variety of techniques, including chemical mutagenesis of isolated DNA, gene amplification by error prone PCR and DNA shuffling, have been employed to generate large libraries of mutant genes, including a few rare mutants expressing the envisaged activity. Multiple rounds of selection and mutagenesis were successfully employed for the isolation of increasingly improved enzymes. Thus, a mutant of $\beta$-lactamase exhibiting a 32,000 fold increase of activity on cefotaxime (W. P. Stemmer, 1994. Rapid evolution of a protein in vitro by DNA shuffling. Nature, 370, 389–391) and the conversion of a galactosidase into fucosidase (J. H. Zhang, G. Dawes and W. P. Stemmer, 1997. Directed evolution of a fucosidase from a galactosidase by DNA shuffling and screening. Proceedings of National Academy of Sciences, USA. 94, 4504–4509) were demonstrated for DNA shuffling. Directed evolution of an esterase into a variant exhibiting higher stability in the presence of water miscible organic solvent (J. C. Moore and F. H. Arnold, 1996. Directed evolution of a para-nitrobenzyl esterase for aqueous-organic solvents. Nature Biotechnology, 14, 458–467) and significant increase of enantioselectivity of lipase (M. T. Reetz, A. Zonta, K. Schmossek, K. Liebeton and K. E. Jaeger 1997. Creation of enantioselective biocatalysts for organic chemistry by in vitro evolution. Angew. Chemie (International) 36, 2830–2832) were successfully demonstrated for error prone PCR.

Accumulating experience in these and related studies indicated that isolation of rare clones producing desired enzymes by plate screening is tedious and impractical when large populations e.g. 100,000 and more have to be individually assayed for envisaged activity. There is a need for an efficient rapid screening method of large libraries for envisaged, sometimes non-biological enzymatic activity, for the exploitation of the potential inherent in the combination of mutagenesis, screening and isolation (M. K. Winson and D. B. Kell, 1997. If you've got it, flaunt it—rapid screening for microbial biocatalysts. Trends in Biotechnology, 15, 120–122).

The present invention contributes to overcome the disadvantages of the prior art and also provides valuable new products heretofore not available.

SUMMARY OF THE INVENTION

The invention provides a methodology for the convenient separation of large cell populations into individual colonies, each derived from a single cell. These colonies are readily assayed in parallel for the desired activity and rapidly screened for the isolation of selected mutants expressing the envisaged activity.

The invention also provides a methodology for the screening of large cell populations for rare mutants expressing a desired product or enzymatic activity. In a preferred embodiment, the method is based on the separation of the cell population into single cells which are adsorbed individually onto the surface of derivitized microbeads. The beads are subsequently immobilized as a monolayer, consisting of single beads or small groups of beads, on a solid surface. The resulting monolayer is, if desired, equilibrated in a suitable growth medium, allowing the immobilized cells to grow and generating immobilized cell colonies, thereby intensifying the signal by that the colonies which have the target activity will be detected. When the enzyme is a highly active enzyme and/or when the assay is a very sensitive assay, it will not be necessary to cause the single cell to grow, and detection can proceed without that step. Following washing, the colonies are equilibrated with a suitable substrate, washed again, then incubated to allow the development of a fluorescent or colored signal. Detection of colonies generating the signal, which are characterized as colored sites in the monolayer, is carried out under optical magnification. Colonies identified on the basis of their color development are subsequently isolated by micromanipulation.

This method offers several major advantages over the alternative screening methods that are currently available: It allows convenient handling of a large cell population divided into separated colonies with cycles of medium treatments with interim washings. The optional complete removal of excess liquid allows testing of these distinctively separated immobilized colony "islands", without product diffusion from one colony to another. It allows very compact handling of a very large cell population confined to a small area of a solid surface e.g. several hundred colonies per cm². There is no need to assay each individual colony: the few very best are readily collected while the massive excess of colonies exhibiting poor or no activity are ignored.

As will become apparent from the description herein, the invention also relates to the identification of novel biocatalysts, e.g., enzymes, preferably genetically engineered biocatalysts with new activities and/or substrate specificity, or biocatalysts that are capable of conducting stereo-specific chemical reactions, or that are capable of conducting reactions under conditions such as extreme pH or temperature, or in organic solvents. The invention can identify genetically engineered biocatalysts unlikely to have been selected for by natural evolutionary processes, i.e., enzymes that are adapted to new demands, or that exhibit features that are not required in nature.

In accordance with the method of the invention, novel biocatalysts can be identified that are capable of carrying out steps in complex chemical syntheses by biotransformation.

Other aspects of the invention will become apparent from the detailed description which follows.

DETAILED DESCRIPTION OF THE INVENTION

Figure 1B:
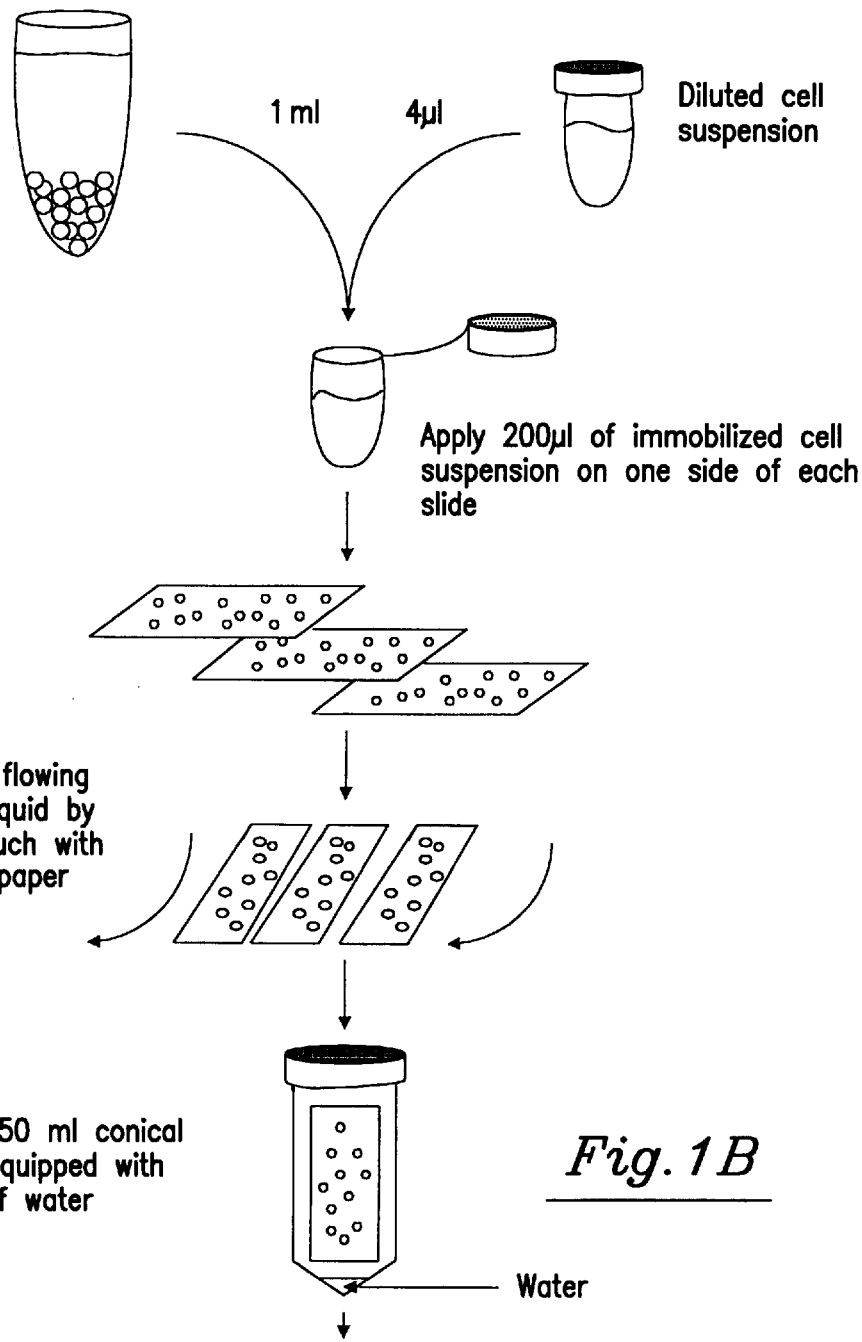
FIG. 1 A–D is a flow diagram describing the process of screening for mutants expressing envisaged hydrolytic activity.

Broadly described, the invention provides a screening method that is useful for identifying a clonal population of cells that exhibit a desired trait, or that express an enzyme possessing a desired activity, from a large mixed population of cells, preferably a randomly mutagenized population of cells. To accomplish this, a native cell population is randomly mutagenized using any of a variety of mutagenesis methods known in the prior art to generate at least one cell that possesses a desired property, for example, a cell that expresses a mutated enzyme that is capable of carrying out a chemical reaction that is not able to be conducted by the native, non-mutated enzyme. The collection of randomly mutated cells is screened to identify those cells or clonal cell populations which exhibit the desired property or enzymatic activity according to the method of the invention. Briefly, the mixed cell population is immobilized onto the surface of derivatized polyacrylamide beads such that ideally each bead contains only a single cell. The beads are subsequently immobilized onto a suitable preferably solid, surface such as glass or metal and, preferably, the cells are made to grow in a cell-growth medium to generate clonal populations on each bead. The clonal populations that exhibit the desired trait are detected visually using an assay which is capable of generating or utilizes a colored or fluorogenic compound, the production or utilization of which is either directly or indirectly dependent upon the presence of the enzymatic activity desired. For example, a direct assay system is illustrated in "A" below:

A) Desired Enzyme+Substrate→Colored Product

This approach requires the addition of a suitable chromogenic or fluorogenic substrate to the immobilized cell population. Action of the desired enzymatic activity upon the substrate generates a colored or fluorescent product which is detected visually. Alternatively, the desired enzymatic activity may generate a colorless or non-fluorogenic product from a colored or fluorogenic substrate. In each case, the presence or absence of the colored or fluorogenic product is directly dependent upon the action of the desired enzymatic activity upon the substrate. It is also possible that the substrate not generate a colored product, but instead its reaction with the enzymatic activity changes the pH of the reaction mixture. Such a change in pH an readily be detected by known indicator dyes, which change color in response to changes in pH.

An indirect assay to detect a clonal cell population exhibiting a desired property or enzymatic activity is illustrated in "B",

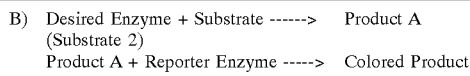

B) Desired Enzyme + Substrate ------> Product A
(Substrate 2)
Product A + Reporter Enzyme -----> Colored Product where the reporter enzyme is a known enzyme that is capable of generating a colored product from Product A. In this approach, the action of the desired enzymatic activity upon a suitable substrate does not generate a colored or fluorogenic product, but produces a compound that functions as a substrate or co-factor for a second reporter enzyme. The action of the reporter enzyme on the intermediate product A generates the colored or fluorogenic product. Product A may represent a substrate for the reporter enzyme that is capable of producing a colored product, or alternatively it may represent a co-factor, e.g., ATP or NADH, required by the reporter enzyme to act on a colorigenic substrate (substrate 2). Thus the presence of the detectable colored product is dependent directly upon the activity of the reporter enzyme, whose activity in turn is dependent upon the action of the desired enzymatic activity upon its substrate.

OTHER EMBODIMENTS

The method of the invention is not restricted to the identification of cells or clonal populations of cells expressing enzymatic activity, but rather can be used to identify cells producing abzymes (antibodies exhibiting catalytic activity), enzyme inhibitors, proteins which are not enzymes, and also non-proteinaceous materials such as carbohydrates. For example, a cell that expresses an inhibitor of a given enzyme can be identified and isolated from a complex mixture of cells if the immobilized beads are pretreated with the targeted enzyme resulting in immobilized enzyme, co-immobilized with the cells. Immobilized cells containing the inhibitor will inhibit the enzyme reaction and block the subsequent production of color. Therefore, beads containing these cells will be colorless whereas beads containing cells without the inhibitor will be highly colored. Thus, the visual selection in this case is based upon the lack of color generation by the desired cells.

Cells expressing other proteins or expressing non-proteinaceous molecules like carbohydrates can also be detected e.g. by the formation of a slimy or turbid appearance. After removal of the primary antibody solution, a fluorescent labeled secondary antibody that recognizes and reacts with the primary antibody is added. Beads containing the desired cells are identified by fluorescence.

DESCRIPTION OF A SPECIFIC EMBODIMENT

More specifically, the invention provides a method for the screening of large cell populations for the isolation of mutants expressing an envisaged (or target) activity like an enzymatic activity. The method of the invention comprises the following stages:

The cells to be screened are mixed with a suspension of an excess number of gel-made microbeads e.g. 45–90 $\mu$m, exhibiting surface properties affecting quantitative cell adsorption upon contact. This step results in a suspension of single cells immobilized onto the surface of microbeads in a mixture with an excess of cell-unoccupied microbeads. Microbeads employed may be pre-equilibrated with appropriate growth medium. The cells to be screened are part of mutated cell populations. The suspension thus obtained is contacted with a solid surface capable of strongly adsorbing the microbeads. This step results in a monolayer of adsorbed microbeads, located either as single, clearly separated microbeads or as small groups (e.g. 3–5) of microbeads. The solution between the adsorbed beads on the solid surface is removed, preferably by applying appropriate means, physical means such as suction or centrifugation or other means that do not affect the viability of the cells.

Thereafter, the support holding the adsorbed microbeads is placed in an appropriate closed vessel and incubated under controlled temperature for cell proliferation into immobilized cell colonies. This proliferation of the cells will cause an amplification of the signal of the target activity exhibited by the target cells. The immobilized cell colonies are then contacted with a substrate and an indicator solution for a period allowing full equilibration with the adsorbed microbeads. The excess of the solution between the beads is subsequently removed and the immobilized colonies are incubated under controlled temperature for signal (e.g. color change) development. Screening for microbeads exhibiting the envisaged visual change is carried out under magnification (e.g. binocular), and selected colonies may be removed using a micro-manipulator (e.g. tip of a sterile needle), under magnification.

OTHER COMPONENTS OF THE SYSTEM OF THE INVENTION

Although the detailed chemical structure of the surfaces of different cell types is variable, all cell surfaces share two common features: a negative surface charge and the presence of hydrophobic elements. The microbeads used in the method of the invention possess a positively charged, partially hydrophobic surface and thus will adsorb many different cell types. Cell populations that are suitable for the screening method of the invention include bacterial, yeast, fungal and mammalian cell populations.

An enzyme possessing the desired catalytic activity, or any desired product, such as an enzyme inhibitor, expressed by individual members of the cell population may be preferably displayed and anchored on the cell surface (J. A. Francisko, C. E. Earhart and G. Georgiou 1992. Transport and anchoring of $\beta$-lactamase to the external surface of *Escherichia coli*. Proceedings of National Academy of Sciences, USA. 89, 2713–2717). However, the detection of intracellular active enzymes or products is within the scope of the present invention, since a substrate can be chosen that will penetrate the cell wall and permit identification of the target activity. In addition, secreted products that exhibit strong adsorption to the microbead matrix are also detected by the assay.

Thus, the method of the invention contemplates detecting and identifying the target activity or product irrespective of its physical location on or in the microbead. One skilled in the art will be able to select or develop the appropriate assay for the identification of the target.

To generate cells that express a desired trait, e.g., an enzyme that catalyzes a non-biological chemical reaction, or an enzyme with altered substrate or reaction specificity, the cell population to be screened is first mutagenized. Mutations may be affected by any method that causes mutations in DNA, including irradiation mutagenesis (e.g., UV), chemical mutagenesis, site-directed (inversion or insertion) mutagenesis, error prone polymerase chain reaction (PCR), DNA shuffling, or a combination thereof.

The microbeads of the invention are preferably of cross-linked polyacrylamide (PAA) that are derivitized by controlled aminolysis to generate primary alkylamine groups, e.g., butylamine or hexylamine, groups on their surface. Controlled aminolysis is well described in the art (S. Reuveny, A. Mizrahi, M. Kotler and A. Freeman 1983. Factors effecting cell attachment spreading and growth on derivatized microcarriers: II Introduction of hydrophobic elements. Biotechnology and Bioengineering, 25, 2969–2980). Reuveny et al. in an earlier article (S. Reuveny, A. Mizzatri, M. Kotler, and A. Freeman, Biotechnol Bioeng., 25, 469 (1982) discussed factors influencing the chemical nature of microcarriers (MC) on cell attachment, spreading and growth. In the 1983 article, the authors report optimum cell growth was reported for the butylamine and hexylamine poly-acrylamide microcarriers. MC carrying primary amino were preferred for further studies since they allowed for cell propagation at relatively low degree of charging. The data presented showed the advantage of using PAA MC derivatized with diaminobutane and diaminohexane. One skilled in the art can from these publications select without undue experimentation the particular derivatized microcarrier, including the amine, the degree of charging and the hydrophobicity best suited for the type of cells to be screened and other objectives sought to be attained.

Suitable derivatized microbeads can be readily made of other polymeric materials which will cause adhesion of the target cells. Illustrative of such polymeric bead-forming polymers are poly(methacrylamide), like Eupergit®, poly (acrylamide), polyamine-methylene substituted resin of diphenol dimethylmethane and formaldehyde in basic form, polycarbonate, polyethylene imine, and other cross-linked phenolics, alkyds, polysaccharides, and polyesters which are derivatized to form the microbeads. These beads have the capacity to have cells adhere to their polymeric structure but will not affect the activity, e.g., viability of the cells and are also inert in the assay.

The ratio of cells to microbeads is not critical as long as there is an excess of microbeads so that ideally one cell will adhere to one microbead and to promote this condition, there will be microbeads which are free of cells. The teachings of the references cited herein are incorporated by reference in their entirety.

The solid support is any material that strongly adsorbs the derivitized beads of the invention. Preferably, the solid support of the invention is glass or a metal (e.g. a stainless steel sheet).

Detection of cell colonies expressing the desired activity or trait is accomplished by identifying colonies that generate a detectable signal that correlates with the generation of the target activity or trait. For practical reasons and convenience, this may be performed by visually identifying those colonies that generate color or fluoresce upon incubation with a suitable substrate for the development of the signal (not to promote the growth of the colonies). Preferably, visual identification of these colonies is carried out under magnification using a binocular microscope. However, detection of positive colonies by digital image analysis or any procedure capable of detecting colored or fluorescent compounds is within the scope of the invention.

The method of the invention may be readily applied to the isolation of mutants and overproducers of strong enzyme inhibitors by adding the target enzyme onto the microbead matrix as immobilized enzymatic activity, to be shut down by irreversible inhibitors secreted by the co-immobilized screened cells. Furthermore, it may be applicable to the isolation of overproducers.

The invention is more specifically illustrated by the following non-limiting examples.

EXAMPLE 1

Isolation of *E. coli* cells displaying surface anchored β-lactamase

The method was applied to the recovery of a known input of β-lactamase expressing *E. coli* cells added into a large excess of *E. coil* cells expressing non enzymatic protein. *E. coli* RB791/pTX101 cells expressing surface anchored β-lactamase via the Lpp-OmpA-protein fusion system were obtained, grown and maintained as previously described (A. Freeman, S. Abramov and G. Georgiou, 1996. Fixation and stabilization of *Eschericia coli* displaying genetically engineered cell surface proteins. Biotechnology and Bioengineering, 52, 625-630). *E coli* JM109 cells displaying an engineered domain (Z) based upon the B domain of staphylococcal protein A, obtained from the plasmid pEZZ18 (Pharmacia Biotech), were similarly prepared displaying the fused protein Lpp(1–9)OmpA(46–159)ZZ.

Figure 1C:
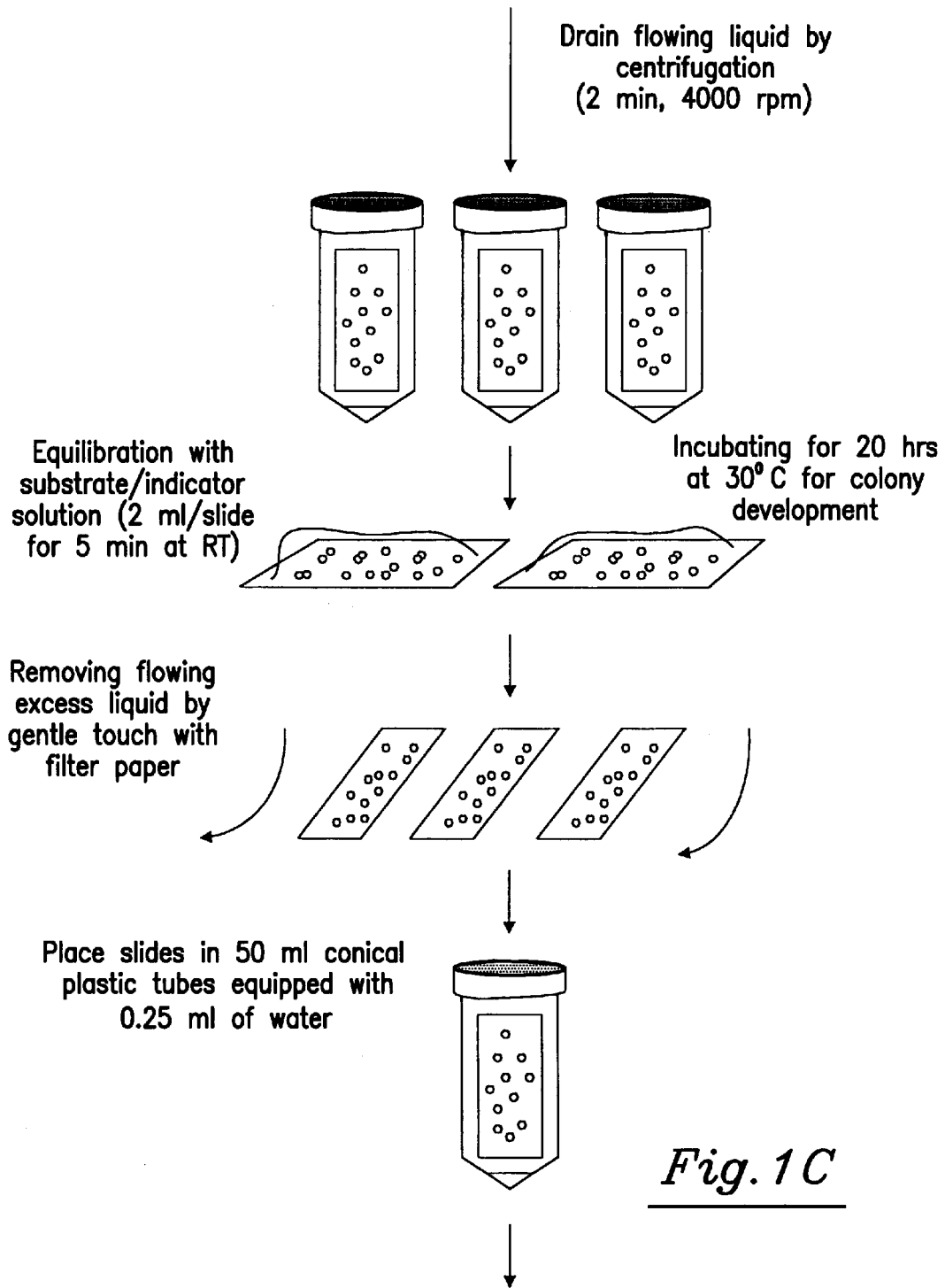

Cells displaying β-lactamase activity were mixed with a 1000 fold excess of the Z domain expressing cells. Polyacrylamide beads (Biogel P-60, Biorad) were chemically modified to butylamine derivative (1.0 meg/g dry weight PAA) as previously described (S. Reuveny, A. Mizrahi, M. Kotler and A. Freeman. 1983. Factors effecting cell attachment spreading and growth on derivatized microcarriers: II Introduction of hydrophobic elements. Biotechnology and Bioengineering, 25, 2969–2980). A 4μl sample of the cell suspension was mixed with the beads suspension as described in FIG. 1A. Pretesting to define cell/bead ratio is performed by equilibrating the bead suspension with growth medium (packed bead total volume ration 1:5–5×10$^5$ beads/nl). The cell suspension accordingly diluted to allow 2:1 bead/cell ratio upon mixing as described in FIG. 1B under "Screening Protocol". There are applied 200 μl of immobilized cell suspension on one side of several clean microscope slides. Following beads adsorption on microscope slides (Chance Proper, UK ) and removal of excess growth medium liquid by centrifugation in a plastic tube containing some water (e.g. 0.25 ml), the immobilized cells were allowed to grow into immobilized cell colonies as described in FIG. 1C. The growth medium was Bacto yeast extract and Bacto Tryptone (see Freeman, et al. (cited). Incubation was for 20 hours at 30° C. until colonies developed. The immobilized cells on the immobilized beads were then equilibrated (2 ml/slide for 5 m. at 25° C.) with substrate and indicator solution (0.8 mg of bromocresol purple and 37.2 mg Penicillin G in 10 ml of 0.2 mM EDTA, pH 8).

Figure 1D:
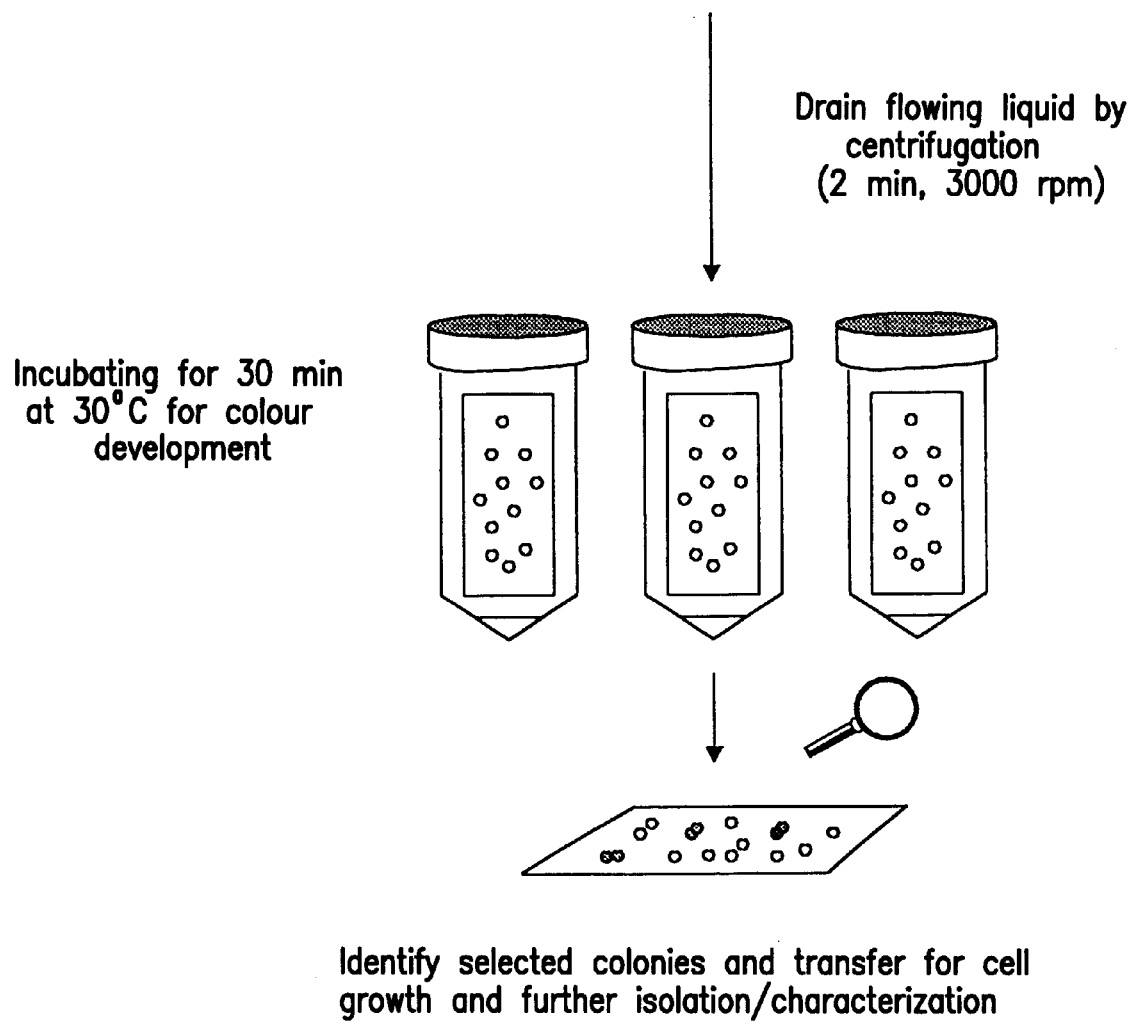

Following removal of excess liquid (by adsorption on filter paper) and incubation for color change development as described in FIG. 1D, the slides were screened under a binocular scope (Zeiss 2000 C) for the identification of yellow colonies. Positive colonies were readily recovered by a 22 guage syringe needle and transferred to plates. Cells grown from these colonies exhibited the same specific β-lactamase activity as the original cell input (growth and activity assays were conducted as previously described (A. Freeman, S. Abramov and G. Georgiou, 1996. Fixation and stabilization of *Eschericia coli* displaying genetically engineered cell surface proteins Biotechnology and Bioengineering, 52, 625–630).

EXAMPLES 2–3

Example 1 is repeated using a cell ratio of 1 to 10,000 and substituting the beads with derivatized Eupergit® beads (polymethacrylamide beads). Comparative results are obtained.

Example 1 is repeated using a cell ratio of 1 to 50,000.

EXAMPLE 4

Identification of β-lactamase using PADAC substrate

The cell mixtures containing β-lactamase described in Example 1 were immobilized onto beads and incubated with growth medium as previously described. Beads containing cells possessing β-lactamase were identified by equilibrating the immobilized beads with 200 μg/ml PADAC (Calbiochem) in 50 mM phosphate, pH 7.5. After removal of the substrate solution, cells expressing β-lactamase were identified by their color change from purple to yellow. After isolation of the cells by micro-manipulation, the cells were shown to have the same specific activity as the β-lactamase expressing input cells.

EXAMPLE 5

Identification of Cells Expressing Alkaline Phosphatase.

To identify cells possessing surface bound alkaline phosphatase from a mixture of cells not expressing the enzyme, cells displaying the engineered domain of protein A (see Example 1) were fixed by glutaraldehyde treatment as described by Freeman et al. (Biotechnology and Bioengineering, 1996, 52:625–630). After washing, cells were suspended in PBS buffer (OD$_{600}$=4) and 3 μl of alkaline phosphatase (Sigma P5221) were added to one ml of the cell suspension. The resulting mixture was shaken at room temperature for 2 hrs. The cells were washed three times with PBS, mixed with untreated cells and immobilized onto microbeads as described in Example 1. Immobilized beads were subsequently equilibrated with a substrate solution consisting of 5-bromo-4-chloro-3-indolyl phosphate and nitro blue tetrazolium. Beads containing the cells expressing alkaline phosphatase were readily detected by the formation of an insoluble purple precipitate.

EXAMPLE 6

The procedure of Example 1 is repeated omitting the measures to cause the cell to develop and multiply on the slides. Though the development of the yellow color will be more faint and slower to develop, identification of the cell is feasible.

When derivatized Eupergit® beads are used selection of the cells can also be performed.

EXAMPLES 7–10

Treatment of Mammalian Cells

Four types of mammalian cells were used for absorption on the derivatized microcarriers as described by Reuveny et al. supra. The cells which were absorbed were hamster kidney established cell lines (BHK), canine kidney (MDCK) established cell line, chick embryo (CEF) primary cells with pronounced fibroblast morphology and human diploid foreskin (FS) cells with pronounced fibroblast morphology (used for the production of beta-interferon).

When cell populations from each one of these four types are subjected to mutagenesis (UV mutagenesis) mixed populations of mutant cells will result. When treated in accordance with the methodology herein described, it is expected that mutant will be identified which exhibit an activity not possessed by the respective native populations.

EXAMPLE 11

Example 1 is repeated on an *E. coli* cell population which had been treated by the DNA shuffling method. The cell libraries are screened for new β-lactamase activity on cephalosporin C, or for amidase activity on (S)-(-)-2-Pyrrolidinone-5-carboxylic acid (synthetic analogue)—or for amidase activity on dimethyl acrylamide (synthetic) unnatural potential substrate, exhibiting very poor resemblance to the natural, original substrate (Pen G).

The substrate to be used is substrate/pH indicator mixtures, all based on the same parent expression system as above described, namely the Lpp-OmpA-protein fusion. Following this method, lactamase activity will be detected.

The teachings of all prior art publications cited herein are incorporated by reference in their entirety.

We claim:

1. A method for identification and isolation of a mutagenized cell or a clonal population of cells having an assayable activity comprising the steps of:
   (a) non-selectively adsorbing substantially an entire mixed cell population onto the surface of derivatized cross-linked polymeric beads under conditions where each bead has either a single immobilized cell adhering to the bead surface, or has no cell adhering thereto;
   (b) adsorbing and immobilizing the beads on a supporting surface;
   (c) removing excess growth medium from the beads;
   (d) equilibrating the beads with a substrate solution wherein said substrate solution produces a signal when acted on by said assayable activity thereby providing evidence of said assayable activity;
   (e) removing excess substrate solution and incubating the beads carrying the cells on the surface of said beads under conditions that will allow the remaining substrate to be acted upon by the assayable activity to directly or indirectly produce evidence of the assayable activity;
   (f) localizing the beads producing evidence of the assayable activity, thereby identifying the cells expressing the assayable activity; and
   (g) isolating the cells producing evidence of the assayable activity by micro-manipulation, thereby forming a clonal population of cells on each bead.

2. The method of claim 1 wherein the beads are polyacrylarnide derivatized beads.

3. The method of claim 2 further comprising the step of incubating said immobilized cells on said beads that have been immobilized on said supporting surface in a growth medium under conditions wherein said immobilized cells proliferate and proceeding to step (c).

4. The method of claim 3 wherein said evidence is visually detectable.

5. The method of claim 4 wherein the assayable activity is an enzymatic activity.

6. The method of claim 5 wherein the evidence of the assayable activity is a color change.

7. The method of claim 6 wherein the mixed cell population is the product of random mutagenesis.

8. The method of claim 7 wherein the polyacrylamide beads are equilibrated with cell-growth medium prior to adsorbing the cells.

9. The method of claim 7 wherein the cell population is bacterial cells.

10. The method of claim 9 wherein a plurality of said beads each have a single immobilized cell on a surface of said bead.

11. The method of claim 10 wherein the visually detected evidence on the beads carrying a single cell on the surface of said bead is performed in parallel on a plurality of beads.

12. The method of claim 9 wherein the assayable activity is detected directly.

13. The method of claim 9 wherein the assayable activity is detected indirectly.

14. The method of claim 7 wherein the cells are mammalian cells.

15. The method of claim 1 wherein said derivatized cross-linked polymeric beads are pre-equilibrated in a liquid medium prior to step (a).

16. The method of claim 1 wherein said conditions of non-selectively adsorbing substantially an entire mixed population onto said surface of said derivatized cross-linked polymeric beads are combining said beads and said mixed cell population at a bead to cell ratio of at least 2:1.

17. The method of claim 16 wherein said bead to cell ratio is at least 4:1.

* * * * *